United States Patent [19]

Harvey et al.

[11] Patent Number: 5,585,506

[45] Date of Patent: Dec. 17, 1996

[54] ONE PHASE PRODUCTION OF POLYGLYCEROL ESTERS

[75] Inventors: Scott B. Harvey, Bethlehem, Pa.; Shilan Shen, High Bridge, N.J.

[73] Assignee: Lonza Inc., Fair Lawn, N.J.

[21] Appl. No.: 279,493

[22] Filed: Jul. 22, 1994

[51] Int. Cl.$^6$ ....................................................... C11C 3/00
[52] U.S. Cl. ............................................................ 554/173
[58] Field of Search ............................................... 554/173

[56] References Cited

U.S. PATENT DOCUMENTS

| | | |
|---|---|---|
| 3,480,616 | 11/1969 | Osipow et al. . |
| 3,644,333 | 2/1972 | Osipow et al. . |
| 3,792,041 | 2/1974 | Yamagishi et al. . |
| 3,963,699 | 6/1976 | Rizzi et al. . |
| 3,996,206 | 12/1976 | Parker et al. . |
| 4,517,360 | 5/1985 | Volpenhein . |
| 4,518,772 | 5/1985 | Volpenhein . |
| 4,611,055 | 9/1986 | Yamamoto et al. . |
| 4,713,436 | 12/1987 | Downs et al. . |
| 4,778,881 | 10/1988 | Nieuwenhuis et al. . |
| 4,790,962 | 12/1988 | Keulemans et al. . |
| 4,868,329 | 9/1989 | Powanda et al. ................ 560/205 |
| 4,973,682 | 11/1990 | Willemse . |
| 5,006,648 | 4/1991 | Van der Plank et al. . |
| 5,071,975 | 12/1991 | Ver der Plank et l. . |
| 5,079,355 | 1/1992 | Meszaros Grechke et al. . |
| 5,144,023 | 9/1992 | Willemse . |

FOREIGN PATENT DOCUMENTS

| | | | |
|---|---|---|---|
| 1185610 | 4/1985 | Canada ........................ | C07C 69/33 |
| 91109949.2 | 4/1992 | China ........................... | C07C 67/08 |

*Primary Examiner*—Gary Geist
*Assistant Examiner*—Deborah D. Carr
*Attorney, Agent, or Firm*—Darby & Darby

[57] ABSTRACT

A semi-batch process for the manufacture of polyglycerol esters by direct fatty acid esterification of a polyglycerol. Molten fatty acid is fed slowly into polyglycerol at a rate which maintains the reaction mixture substantially homogeneous. Improved quality of the resultant polyglycerol esters and shorter reaction cycles are thereby realized.

19 Claims, No Drawings

ONE PHASE PRODUCTION OF POLYGLYCEROL ESTERS

BACKGROUND OF THE INVENTION

Polyglycerol esters, per se, are well known in the art. They have various uses, such as components of cleansing, bath, and shampoo compositions, and as cosmetics and food additives.

Conventionally polyglycerol esters are manufactured in a batch process starting with a two-phase reaction mixture: a polyglycerol phase (hydrophilic) and a fatty acid phase (lipophilic). When the mixture is heated, the esterification reaction occurs at the interface of the two phases, initially yielding a highly substituted polyglycerol ester. High temperatures and extended mixing periods are necessary to effect the redistribution of the ester groups from the highly substituted ester to the unreacted polyglycerol, commonly referred to as transesterification. It is only when the transesterification is completed that the reaction mixture becomes the desired clear, single-phase solution.

Other examples of known processes for producing polyol fatty acid esters are:

(1) U.S. Pat. Nos. 3,963,699 and 4,517,360 assigned to The Procter & Gamble Company. Both relate to a transesterification process where a homogeneous reaction melt of a polyol, a fatty acid lower alkyl ester, an alkali metal fatty acid soap, and a basic catalyst is first formed. Additional fatty acid lower alkyl esters are added to the product of the initial step to produce polyol fatty acid polyesters. Such processes use fatty acid lower alkyl esters (rather than fatty acids) and transesterification rather than direct esterification.

(2) U.S. Pat. Nos. 5,006,648, 5,071,975, and 5,079,355 assigned to Van den Bergh Foods Co. The first two patents teach processes for preparing highly substituted polyol fatty acid esters (and lower substituted esters) by mixing a polyol with an alkaline catalyst to prepare a first reactant mixture, mixing a fatty acid lower alkyl ester with a fatty soap to prepare a second reactant mixture, and thereafter blending the two mixtures. The reaction is conducted at the relatively low temperature of 100°–180° C. due to the relatively high soap levels used.

U.S. Pat. No. 5,079,355 discloses a transesterification process wherein a mixture of polyol, fatty acid lower alkyl ester, transesterification catalyst, and alkali metal soap is reacted under transesterification conditions,

BRIEF DESCRIPTION OF THE INVENTION

The present process may be characterized as a "one phase" or "semi-batch" process for the production of polyglycerol esters. A suitable polyglycerol is preheated and dehydrated. A molten $C_6$ to $C_{22}$ fatty acid is thereafter slowly fed in a controlled manner into the polyglycerol so as to maintain the mixture homogeneous while forming the desired polyglycerol ester product. The reaction mixture is cooled and the product polyglycerol ester recovered.

The present process significantly improves product quality, especially the color, taste, and odor of the product. The need for high levels of alkali metal soap (as an emulsifier) and the time required to achieve reaction equilibration typical of the two phase batch processes of the prior art is substantially reduced or eliminated. Compared to a low soap batch process, the reaction temperature can be reduced and product quality enhanced. Additionally, the generation of methanol, found in the prior art transesterification process, and it attendant disposal problems, are avoided.

DETAILED DESCRIPTION OF THE INVENTION

The essential components, their relevant proportions, and the reaction conditions of the invention are set forth below. Unless otherwise indicated, all percentages are on a weight basis. All patents, publications and test methods mentioned herein are incorporated by reference.

As used in the present specifications, the term "fatty acid" is intended to include $C_6$ to $C_{22}$ fatty acids, both saturated and unsaturated.. Preferred saturated fatty acids include lauric, stearic, palmitic, behenic, myristic, caprylic, capric, caproic and arachidic. Preferred unsaturated fatty acids include myristoleic, linoleic, oleic, licanic, ricinoleic, linolenic, eleostearic and erucic. The fatty acid may have a straight or branched alkyl chain and may be used singly or as admixtures thereof.

As used herein, the terms "polyol" or "polyglycerol" denote polymers of glycerin with hydroxyl values corresponding to 2 to 10 glycerine monomers per chain. Examples include diglycerol, triglycerol, tetraglycerol, pentaglycerol, hexaglycerol, octaglycerol, nonaglycerol and decaglycerol.

In contrast to the product obtained from the batch process heretofore used, the product of the semi-batch process of the invention has noticeably better color, namely, 2 to 3 on the Gardner Scale. The difference in taste and odor profiles of the two products is dramatic. The semi-batch product has a much better taste and odor profile than the 1.5 batch product. In fact, the semi-batch product was very similar to the product obtained from conventional batch processing wherein the polyglycerol is initially ion-exchanged.

As compared to the prior batch process, the above process proceeds efficiently at a temperature of 20° to 25° less. Lower temperatures are effective because the transesterification process, which requires high temperatures, was eliminated. These lower reaction temperatures translate directly into improved product quality and shorter heat-up times.

By maintaining a single phase reaction mixture throughout the process, mass transfer is no longer the limiting factor in completing the reaction and the reaction scheme is far simpler. In addition, the process of the invention is more reproducible and fatty acid carryover is reduced. In the prior process, the fatty acid frequently co-distilled with the dilution water in the polyglycerol. In the instant case, the fatty acid, when metered into the process, reacts almost instantaneously; thus, its concentration in the reaction medium is always extremely low. This results in higher yields and reduced waste loading.

By dehydrating the polyglycerol prior to fatty acid addition, in effect, extra reactor volume is obtained. Also, dehydrating prior to fatty acid addition allows for more flexibility in the polyglycerol dilution level. Higher dilution levels are frequently desired for more effective carbon treatment of the polyglycerols. This would translate into reduced capacity in the batch process, but not with the semi-batch process.

Finally, the shorter heat-up time and the elimination of the transesterification cycle markedly reduce cycle times. A 2 to 3 hour reduction is typical.

The optimum reaction temperatures and pressures will be dependent on the particular polyglycerol esters being prepared. Broadly, the temperatures will be in the range of from 210° to 260° C., and the pressures in a range of from 25 to 760 mm Hg abs. While it is preferable that the fatty acid be added at a uniform rate during the course of the reaction, intermittent addition may also be used, the main purpose being to avoid any substantial build-up of fatty acid in the reactor. Generally, the addition time is at least ½ hr., most desirably at least 2 hrs.

The mode of addition of the fatty acid is also an important consideration. Preferably, subsurface feed is used, though the fatty acid may be added to the surface of the liquid in the reactor. The disadvantage is that noticeably more fatty acid is carded over to the condenser. Additionally, it is not necessary to heat the fatty acid prior to introduction, so long as the reactor is able to supply sufficient heat to maintain a constant temperature, including the heat of vaporization for the water of reaction.

While reduced pressures are advantageous in removing the water of condensation, it is preferable not to decrease the pressure below 25 mm Hg so as to avoid any possible boil-up of the fatty acid and further polymerization of the polyglycerol. In addition, high vacuums increase the tendency for air to enter the reactor. This, too, is undesirable. A key factor in determining the optimum pressure is the clarity of the reaction system. The formation of haze within the system is an indication that there is a tendency for a two-phase reaction system to form. Obviously, for the reasons noted above, this is undesirable.

It is important in the process of the invention that the polyglycerol be heated to the reaction temperature and dehydrated prior to the addition of the fatty acid. Upon introduction to the reactor, approximately 20 wt. % of dilution water in the charge will be evaporated. At atmospheric pressure, dilution water is boiled off when the polyglycerol is at a temperature between 105° and 130° C. Care must be taken to avoid further polymerization of the polyglycerol.

After the entire fatty acid charge is added, it is necessary to cook the reactants for an additional period of time. Since the reaction takes place in a single phase, the fatty acid reacts almost immediately. However, to ensure completion of the process, a brief cooking time (as, for example, from 20 to 180 mins.) may be used, preferably about 30 to 40 min. Excessive cooking tends to degrade the color, taste and odor of the product.

A wide variety of catalysts may be used. Most commonly, alkaline materials such as alkali metal carbonates and hydroxides and alkaline earth metal carbonates and hydroxide may be used. Specific examples include sodium and potassium hydroxides and carbonates. Such catalysts may be added directly or carried forward from prior processing steps. Generally, the catalyst level is from 0.1 to 5 mol. %, based on the glycerine used to prepare the polyglycerol. Most preferably, from 0.5 to 2.25 mol. % should be used.

The following is a tabular summary of the key process conditions for the practice of the present invention:

EXAMPLE 1

Preparation of Decaglyceryl Dipalmitate

A high purity tasteless and odorless decaglycerol solution having a Gardner Color of a maximum of 7, a hydroxyl number of 696 to 720 and a 19 to 21% water content is fed to a reactor and vacuum-purged at a pressure of 5 to 25 mm Hg. The vacuum is broken by the introduction of nitrogen into the reactor. A light subsurface nitrogen sparge is used throughout the process to deter air leakage. The decaglycerol solution is thereafter rapidly heated to a temperature of from 210° to 260° C., preferably from 220° to 245° C. While the pressure is not critical, it is preferable to maintain atmospheric pressure at this stage. The dilution water, during this step, boils off at a temperature in the range of 110° to 125° C.

Once the reactor achieves the desired reaction temperature, the pressure is dropped to 50 mm Hg absolute. Rapid pressure drop is best avoided, to eliminate any tendency towards foaming. The reactor is held at the reaction temperature and pressure for a period sufficient to ensure that the polyglycerol has been totally dehydrated. When the vapor temperature drops below the boiling point of water at 50 mm Hg (38° C.), it can be assumed that the polyglycerol is adequately dehydrated.

At this stage, palmitic acid, vacuum-purged and preheated to at least 100° C., is metered into the reactor at a constant rate over a period of three hours. It is added below the liquid surface in the reactor and well dispersed by agitation.

By means of conventional temperature control techniques, the reaction temperature is maintained. After all of the palmitic acid is added, the reaction pressure can be slowly increased to atmospheric pressure. One and one-half hours after the addition of the fatty acid, the product is sampled for refractive index, acid value, hydroxyl number and saponification value. Heating is continued until product specifications are achieved. Thereafter the product is cooled. The finished product has a refractive index of 1.467 on the butyro scale, an acid value of 0.2, a hydroxyl number of 430, and a saponification value of 88.

EXAMPLE 2

Preparation of Hexaglyceryl Distearate

Following the basic procedure described in Example 1, hexaglycerol distearate was prepared by the semi-batch process of the invention. The hexaglycerol used had a hydroxyl number of about 970 and the glycerine levels were in the 4 to 6 wt. % range. The reactions were run at 230° C. and 50 mm Hg pressure with a slight nitrogen sparge. An Anchor stirrer spinning at 250 rpm provided the agitation. Two moles of stearic acid per mole of hexaglycerol were

TABLE A

| PROCESS CONDITIONS | | |
| --- | --- | --- |
| | BROAD RANGE | PREFERRED |
| Preheating of polyglycerol solution °C. | 210 to 260 | 220 to 245 |
| Vacuum for polyglycerol dehydration, mm Hg | 25 to 760 | 50 to 400 |
| Reaction temperature, °C. | 210 to 260 | 220 to 245 |
| Reaction pressure, mm Hg | 25 to 760 | 50 to 400 |
| Addition period for fatty acid at constant rate, hrs. | 0.5 to 5 | 1 to 3 hrs. |
| Molar Ratio of Fatty Acid to Polyglycerol | 0.5:1 to 10:1 | 1:1 to 3:1 |

The following examples further illustrate the process of the present invention.

added over a period of 3 hrs. and the reactants permitted to cook for 1.5 hrs. thereafter. The reaction mixture contained 1 mole of potassium hydroxide, based on the glycerine used to prepare the hexaglycerol, which served as a catalyst. During the course of the fatty acid addition, clouding was initially noted; however, this cleared during the course of the addition and the reaction mixture remained clear during the cooking step. The finished product had a Gardner Color in the 3 to 4 range, a refractive index of 1.4705 on the butyro scale, an acid value of less than 0.1, a hydroxyl number of 255, and a saponification value of 124.

EXAMPLE 3

Preparation of Triglyceryl Monostearate

Following the procedure generally outlined in Example 1, triglycerol monostearate was prepared by the semi-batch process of the invention. The triglycerol had a hydroxy number of approximately 1160 and a glycerine content of about 11 wt. %. The reaction temperature was maintained at 230° C., the reaction pressure at 50 to 100 mm Hg, and the stearic acid added constantly over a period of 3 hrs. The reaction mixture was agitated at 250 rpm by an Anchor stirrer. A slight nitrogen sparge was used to deter air leakage into the reactor.

Until about 75 % of the fatty acid was added, the reaction mixture appeared cloudy; thereafter the mixture cleared and remained clear until the end of the fatty acid addition and for the first 30 min. of the cooking cycle. After 30 min. of the cooking cycle, the batch became slightly turbid; this was cleared by raising the temperature to 235° C.

The overhead water, both that added during dilution and reaction water, was analyzed for glycerine. About 2 % of glycerine was detected. This corresponds to roughly 0.5 wt. % of the starting polyglycerol. This run clearly shows the efficacy of the instant invention for the preparation of esters of high molecular weight polyglycerols. The molar ratio of the triglycerol to stearic acid was 1:1. The refractive index was 1.4701 on the butyro scale, the acid value less than 0.1, the hydroxyl number 310, and the saponification value 138.

We claim:

1. A process for preparing polyglycerol esters which comprises:
    (a) feeding a molten fatty acid at elevated temperature into a polyglycerol at a substantially constant rate over a period of 0.5 to 5 hours, with mixing and at a pressure of between 50 and 400 mm Hg, so as to maintain the reaction mixture in a substantially homogeneous state substantially without formation of separate phases containing said polyglycerol and said fatty acid;
    (b) cooking the reaction mixture in the presence of a basic catalyst for a period of at least 20 min. after the addition of said fatty acid;
    (c) cooling the reaction mixture; and
    (d) recovering the polyglycerol ester product, wherein the molar ratio of said fatty acid to said polyglycerol is such that said polyglycerol ester product is not fully esterified.

2. The process of claim 1 wherein said polyglycerol is a polymer of glycerol with a hydroxyl value corresponding to 2 to 10 glycerine units per chain.

3. The process of claim 1 wherein said fatty acid is a $C_6$ to $C_{22}$ fatty acid.

4. The process of claim 1 wherein reaction temperature is from about 220° to 245° C.

5. The process of claim 1 wherein said polyglycerol is dehydrated under vacuum prior to the addition of molten fatty acid.

6. The process of claim 1 wherein the molten fatty acid is added below the surface of the polyglycerol.

7. The process of claim 1 wherein the polyglycerol is decaglycerol, the fatty acid is palmitic acid, and the polyglycerol ester produced is decaglycerol dipalmitate.

8. The process of claim 1 wherein said fatty acid is selected from the group consisting of lauric acid, stearic acid, palmitic acid, behenic acid, myristic acid, caprylic acid, capric acid, caproic acid, arachidic acid, myristoleic acid, linoleic acid, oleic acid, licanic acid, ricinoleic acid, linolenic acid, eleostearic acid, and erucic acid.

9. The process of claim 1 wherein said polyglycerol ester product exhibits color properties that rate from 2 to 3 on the Gardner scale.

10. The process of claim 1 wherein said fatty acid is fed into said polyglycerol over a period of at least 2 hours.

11. A process for preparing polyglycerol esters which comprises:
    (a) preheating and dehydrating a polyglycerol having a hydroxyl value corresponding to from 2 to 10 glycerine units per chain;
    (b) slowly feeding a molten $C_6$ to $C_{22}$ fatty acid into said polyglycerol at a pressure of between 50 and 400 mm Hg in a reaction zone so as to maintain the reaction mixture in a substantially homogeneous state and substantially
    without formation of separate phases containing said polyglycerol and said fatty acid; and
    (c) cooling the reaction mixture and recovering the polyglycerol ester product, wherein the molar ratio of said fatty acid to said polyglycerol is such that said polyglycerol ester product is not fully esterified.

12. The process of claim 11 wherein reaction occurs at a temperature of 220° to 245° C.

13. The process of claim 11 wherein said fatty acid is fed into the polyglycerol over a period of 0.75 to 3 hours.

14. The process of claim 11 wherein said polyglycerol is dehydrated to a moisture content of less than 0.5 wt, % prior to reacting with said fatty acid.

15. The process of claim 11 wherein the molar ratio of fatty acid to polyglycerol fed to the reaction is in the range of 1:1 to 4:1.

16. The process of claim 11 wherein said $C_6$ to $C_{22}$ fatty acid is fed below the surface of the polyglycerol.

17. The process of claim 11 wherein said fatty acid is selected from the group consisting of lauric acid, stearic acid, palmitic acid, behenic acid, myristic acid, caprylic acid, capric acid, caproic acid, arachidic acid, myristoleic acid, linoleic acid, oleic acid, licanic acid, ricinoleic acid, linolenic acid, eleostearic acid, and erucic acid.

18. The process of claim 11 wherein said polyglycerol ester product exhibits color properties that rate from 2 to 3 on the Gardner scale.

19. The process of claim 11 wherein said fatty acid is fed into said polyglycerol over a period of at least 2 hours.

* * * * *